United States Patent [19]

Lee et al.

[11] Patent Number: 5,375,372

[45] Date of Patent: Dec. 27, 1994

[54] BICOMPONENT TISSUE AND SEEDLING CULTURE BOTTLE

[76] Inventors: Tso-Cheng Lee, No. 16, Pin San St., Pu Li, Nan-Tou; Cheng-Hao Wang, No. 9, Song Shan Hsiang,, Yu Chih Hsiang, Nan Tou; Tsun-Thin Huang, No. 3, Lane 78, An Ho Road 1 Sec., Taipei; Meng-Ta Chen, No. 76, Szu We Hsiang, Fu Chun Road, Tsao Tun, Nan Tou, all of Taiwan, Prov. of China

[21] Appl. No.: 139,738

[22] Filed: Oct. 22, 1993

[51] Int. Cl.⁵ .............................................. A01G 9/14
[52] U.S. Cl. .............................................. 47/69; 47/60
[58] Field of Search .................... 47/69, 60 NL, 60 W

[56] References Cited

U.S. PATENT DOCUMENTS

| | | | |
|---|---|---|---|
| 2,950,567 | 8/1960 | Newman | 47/69 |
| 3,903,642 | 9/1975 | Yellin | 47/69 |
| 4,291,494 | 9/1981 | Knablein et al. | 47/60 NL |

FOREIGN PATENT DOCUMENTS

| | | | |
|---|---|---|---|
| 1188932 | 3/1959 | France | 47/69 |
| 7614174 | 6/1977 | Netherlands | 47/60 NL |

*Primary Examiner*—Ramon S. Britts
*Assistant Examiner*—Joanne C. Downs
*Attorney, Agent, or Firm*—Pro-Techtor International

[57] ABSTRACT

A bicomponent tissue and seedling culture bottle includes an upper cover portion having an opening facing downward, and a lower container portion having a closed base and suitable for fitly but detachably connecting to the downward opening of the upper cover portion, characterized in that, a T-shaped air vent consisting of a vertical air passage centered at a top portion of the upper cover and two horizontal air passages symmetrically located at and extending from two opposite sides of the vertical air passage to be communicable with the outside air, so that air or gas produced in the culture bottle during the culture process can escape from the air vent and germs or viruses can be prevented from entering into the culture bottle when the seedlings are matured and/or are transplanted and the survival percent of the bottle cultured seedlings can be raised.

4 Claims, 3 Drawing Sheets

BICOMPONENT TISSUE AND SEEDLING CULTURE BOTTLE

BACKGROUND OF THE INVENTION

The present invention relates to a tissue and seedling culture bottle, and more particularly to a bicomponent culture bottle having an upper portion which eliminates the conventional narrow bottle mouth and cap and has an improved and integrally formed top air vent so that the culture bottle can be effectively manufactured with less material and a simpler process while the rate of infected and damaged seedlings can be largely reduced.

In order to be more easily exposed under the sunshine and to stand high temperature sterilization, most of the conventional tissue and seedling culture bottles are made of glass. To facilitate the sealing of such culture bottle, the bottle usually has a smaller upper opening and a wider lower base and is integrally formed, as shown in FIG. 1. In the process of tissue culture, the filling of culture medium, the sterilization, the transplantation of seedling, and the removal of the bottle cultured seedlings from the culture medium, are accomplished through the bottle mouth which is about 3.5 cm in diameter. To avoid difficult bacteria-free sealing, the upper opening of the culture bottle can not be enlarged and has to be some distance away from the bottle cultured seedlings or seedling base. All of these are inconvenient to the tissue culture for the following reasons:

a. Seedlings cultured in the culture bottle are dense and vulnerable and therefore must be removed out of the bottle with forceps by experienced and skilled operators to reduce the percentage of damaged seedlings;

b. The seedlings must be removed from the culture bottle with great care and therefore the removal is time-consuming and inefficient;

c. The seedlings removed out of the culture bottle are easily damaged and infected by bacteria or viruses that reduces the survival percent of the bottle cultured seedlings and slows down the growth of seedlings in early stage; and d. In order to prevent the loss of bottle cultured seedlings, people can break the culture bottle to take out all the seedlings from the bottle at one time. However, this causes environmental pollution and increases the cost of cultivation.

To improve the above-mentioned shortcomings existing in the conventional tissue and seedling culture bottles, the applicant invented a "Bottle For Cultivating Seedlings" which has been granted a Taiwan patent and filed in U.S.A. with a Ser. No. 07/868,435. The bottle according to that previous invention has been largely adopted by many professional seedling culture organizations and farms and is found to effectively meet the functions intended by the invention and largely eliminates the shortcomings in the conventional seedling culture bottles. In a series of subsequent and consistent observations, the applicant finds the critical key point to a successful culture of tissue and seedlings is the effective control, prevention, and interception of invasion of bacteria and viruses into the culture bottle during the culture. Among many factors of infection, the poor sealing of the upper opening of culture bottle and the air vents in the culture bottle cap is an important one. That is, there are still other disadvantages existing in the conventional culture bottles in addition to the above-mentioned ones:

1. For a conventional culture bottle 1, when it is filled with the culture medium 11 and is subjected to high temperature sterilization or is exposed to and heated by the sunshine, the air inside the bottle becomes high-pressure gas 12 which applies force on the bottle cap 13 and pushes the same outward. A gap 14 is then formed between the cap and the bottle mouth. The gap 14 is an access point for the bacteria and viruses to the culture medium.

2. The conventional culture bottle 1 usually has an upper opening, a cap, and all the air vents in the cap are facing upward. Apart from the cap 13 that tends to be infected by the bacteria and viruses due to the reason as described in the above item 1, a circle of recess 15 at the joint of bottle mouth 10 and the cap 13 also tends to be covered by built dust or dirt and forms a source of infection. A sheet of clear plastic cloth or cellophane is usually used to wrap the cap 13 for effectively sealing the bottle mouth. This surely increases the material cost.

The above disadvantages were not considered in my previous invention and the upper portion thereof has a structure similar to that of a conventional culture bottle.

It is therefore an objective of the applicant to develop an improved tissue and seedling culture bottle to eliminate the above shortcomings and disadvantages existing in the conventional culture bottles.

SUMMARY OF THE INVENTION

It is a primary object of the present invention to provide a bicomponent tissue and seedling culture bottle having an upper portion which provides one single opening and an air vent free from any accumulated dirt or dust so that the tissue and seedling culture can be conducted in an easier and safer manner.

Another object of the present invention is to provide the above bicomponent tissue and seedling culture bottle in which the upper part is integrally formed without any top bottle mouth so as to simplify the operational procedures in the culture and save the use of the bottle cap.

A further object of the present invention is to provide the above bicomponent tissue and seedling culture bottle in which a T-shaped air vent is formed on top of the bottle so as to reduce the internal air pressure of the heated culture bottle and to prevent dust or dirt from accumulating in the air vent so that the culture bottle can be more effectively sterilized and disinfected and prevents bacteria and viruses from entering the bottle.

BRIEF DESCRIPTION OF THE DRAWINGS

A more complete understanding of these and other features and advantages of the present invention will become apparent from a careful consideration of the following detailed description of certain embodiments illustrated in the accompanying drawings wherein.

DETAILED DESCRIPTION OF THE PREFERRED EMBODIMENTS

Figure 1:
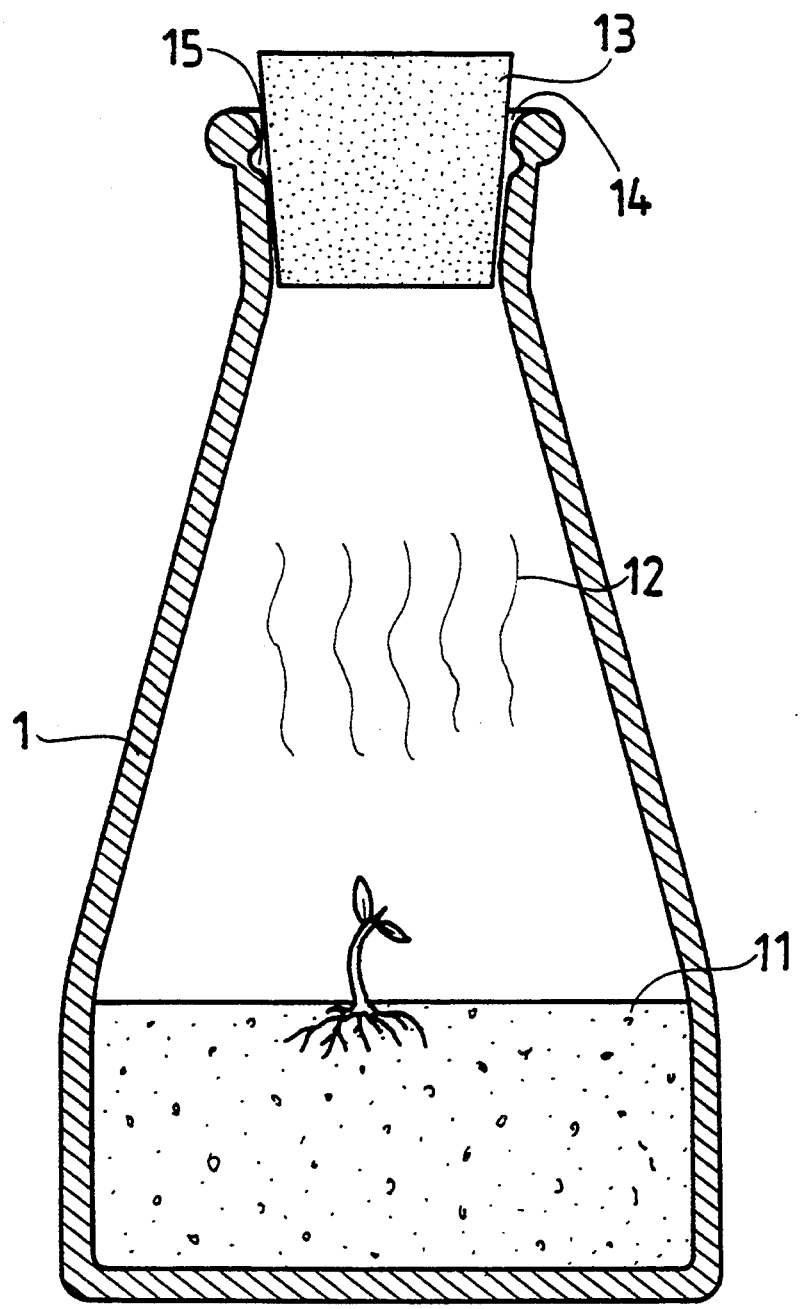
FIG. 1 is a vertical sectional view of a conventional tissue and seedling culture bottle.
Figure 2:
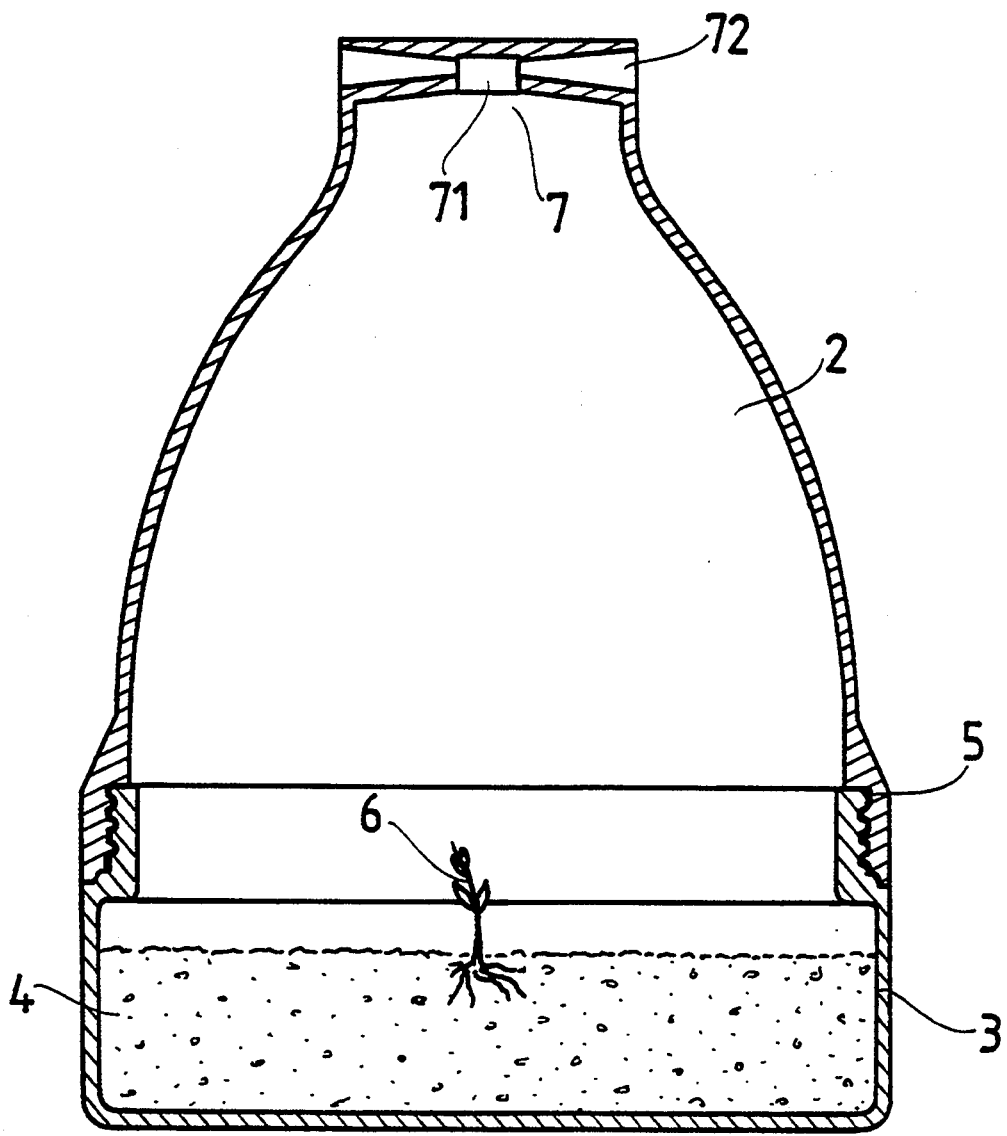
FIG. 2 is a vertical sectional view of the bicomponent tissue and seedling culture bottle according to the present invention.

Please refer to FIG. 2. The present invention includes a conical-shaped upper cover portion 2 having a smaller closed top and a wider lower opening internally threaded, and a lower container portion 3 having an upward opening externally threaded and a closed bottom. The upper cover portion 2 can be tightly but detachably connected to the lower container portion 3 by screwing its internally threaded lower opening to the externally threaded upper opening of the lower container portion 3. It is to be understood that any other fastening means can be used to detachably connect the upper portion 2 to the lower portion 3 of the present invention. A soft rubber seal 5 can be used as an interface between the upper portion 2 and the lower portion 3 to effectively seal the entire connected bottle. The full height of the lower portion 3 is always larger than that required to contain enough culture medium 4.

The upper portion 2 of the present invention can be made of glass, PC, PET, or other transparent or translucent plastic materials, depending on the plants to be cultivated and other practical necessities. The lower portion 3 can be made of glass, PC, PET, or other plastic materials.

When the upper portion 2 is formed by injection molding, a top portion thereof is allowed to have a larger thickness so that a substantially T-shaped air vent 7 having a vertical air passage 71 and two horizontal air passages 72 is formed therein at the same time when the upper portion 2 is injection molded, it also can be formed by means of drilling after the upper portion 2 is formed. The vertical air passage 71 of the air vent 7 is centered at the close top portion with its open end facing downward toward the bottle and has a depth about two-thirds of the thickness of the close top portion of the upper portion 2. The two horizontal air passages 72 are communicable with the vertical air passage 71 and are symmetrically located at any two opposite sides of the vertical air passage 71 at the same height so that they extend straight through the top portion of the upper portion 2 to communicate with the outside air.

Figure 3:
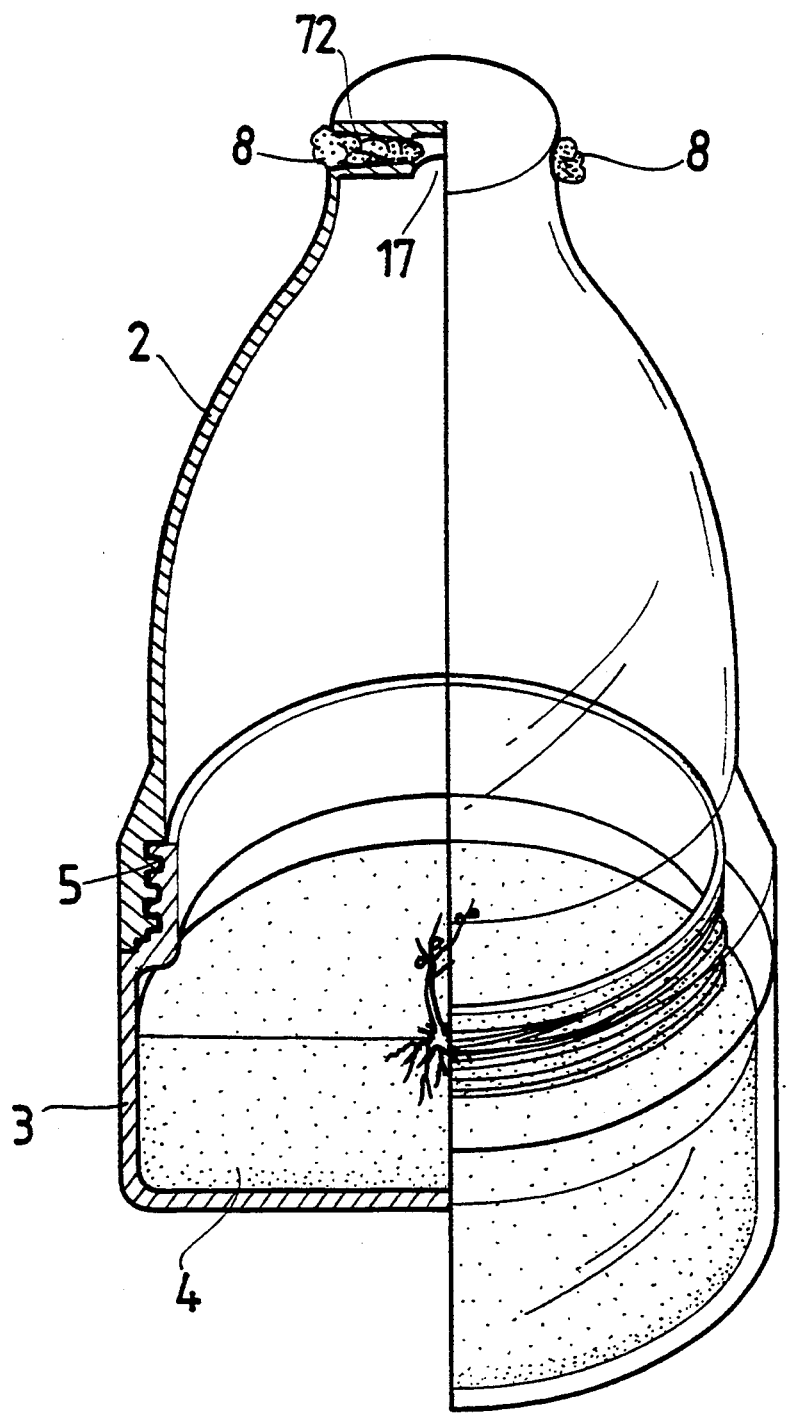
FIG. 3 illustrates an embodiment of the present invention with a portion thereof being taken away to show the connection of the upper and lower parts in a clearer manner.

FIG. 3 illustrates an embodiment of the present invention. To use the tissue and seedling culture bottle according to the present invention, first, the upper portion 2 is removed from the lower portion 3, then the procedures of filling the culture medium 4, high temperature sterilization, and placement of the seeds are performed; after that, the horizontal air passages 72 of the T-shaped air vent 7 on the top of the upper portion 2 are filled with sterilized absorbent cotton 8 to prevent bacteria and viruses from entering into the culture bottle through the air vent 7. When the buds have matured and can be transplanted, the culture bottles are moved to a bacteria-free room for separating the upper portion 2 from the lower portion 3. Subsequently, the buds are then carefully withdrawn out of the lower portion 3 with forceps and transplanted to another seedling culture bottle containing culture medium.

When the lower portion 3 is filled with the culture medium 4, sterilized at high temperature and sowed, the seeds grow in a culture bottle which is very well sealed, being an integrally formed bottle having only one top air vent. From the T-shaped air vent 7 on top of the upper portion 2, the high-pressure gas formed during the high temperature sterilization or exposure to sunshine can escape via the vertical air passage 71, the horizontal air passages 72, and the sterilized absorbent cotton 8 in the air passages 72. In this manner, the bottle cultured seedlings 6 are always protected under a bacteria-free condition during their growth and transplantation and therefore have a higher survival percentage.

It can be seen from the above description that the bicomponent tissue and seedling culture bottle according to the present invention has the following improvements:

1. No cap is needed for the culture bottle;
2. The procedures of seedling culture are simplified;
3. Material and costs required by the culture bottle are reduced; and
4. Infections by germs and viruses can be effectively prevented.

Although the present invention has been described with a certain degree of particularity, the present disclosure has been made by way of example and changes in details of structure may be made without departing from the spirit thereof.

What is claimed is:

1. A bicomponent tissue and seedling culture bottle, comprising:
   a conical-shaped upper cover portion having a closed top end and an open lower end, the top end being smaller than the lower end; and
   a lower container portion for containing culture medium therein and suitable for detachably and tightly connecting to said upper cover portion at said lower open end thereof;
   said upper portion being characterized by an air vent formed on said top end thereof, said air vent including a vertical air passage centered at said top end of said upper cover portion and at least one horizontal air passage extending from said vertical air passage, said horizontal air passage being in communication with said vertical air passage and with the outside air, said air vent allowing air and gas produced in said culture bottle during seedling culture or growth in said culture bottle to escape from said air vent while bacteria and viruses are prevented from entering said culture bottle, thereby increasing the survival percentage of seedlings in said culture bottle.

2. The culture bottle as claimed in claim 1 wherein:
   said vertical air passage and said horizontal air passage form a T-shaped air vent.

3. The culture bottle as claimed in claim 1 wherein:
   a soft rubber seal is disposed at a joint between said upper cover portion and said lower container portion to enhance the sealing of the upper and lower portions.

4. The culture bottle as claimed in claim 1 wherein:
   said upper cover portion and said lower container portion are tightly connected to each other by means of sealing elements.

* * * * *